United States Patent [19]

Berg

[11] Patent Number: 5,718,809
[45] Date of Patent: Feb. 17, 1998

[54] SEPARATION OF T-AMYL ALCOHOL FROM 2-METHYL-1-PROPANOL BY EXTRACTIVE DISTILLATION

[76] Inventor: Lloyd Berg, 1314 S. 3rd Ave., Bozeman, Mont. 50715

[21] Appl. No.: 841,923

[22] Filed: Apr. 8, 1997

[51] Int. Cl.$^6$ .............................. B01D 3/40; C07C 29/84
[52] U.S. Cl. .............................. 203/57; 203/58; 203/59; 203/60; 203/62; 203/64; 203/69; 568/913
[58] Field of Search .............................. 203/57, 58, 59, 203/60, 62, 64, 69; 568/913

[56] References Cited

U.S. PATENT DOCUMENTS

| | | | |
|---|---|---|---|
| 4,416,734 | 11/1983 | Jacobs | 203/18 |
| 4,693,787 | 9/1987 | Berg et al. | 203/57 |
| 4,693,788 | 9/1987 | Berg et al. | 568/913 |
| 4,756,803 | 7/1988 | Berg et al. | 568/913 |
| 4,935,103 | 6/1990 | Berg et al. | 203/57 |
| 5,338,410 | 8/1994 | Berg | 203/63 |
| 5,360,520 | 11/1994 | Berg | 203/58 |
| 5,645,695 | 7/1997 | Berg | 203/57 |
| 5,658,435 | 8/1997 | Berg | 203/57 |

FOREIGN PATENT DOCUMENTS 0047204  3/1982  European Pat. Off. ............ 203/57

*Primary Examiner*—Virginia Manoharan

[57] ABSTRACT

T-Amyl alcohol and 2-methyl-1-propanol are difficult to separate by conventional distillation or rectification because of the proximity of their boiling points. T-Amyl alcohol can be easily separated from 2-methyl-1-propanol by extractive distillation. Effective agents are N,N-dimethylacetamide, cyclohexyl amine and glycerol.

1 Claim, No Drawings

SEPARATION OF T-AMYL ALCOHOL FROM 2-METHYL-1-PROPANOL BY EXTRACTIVE DISTILLATION

FIELD OF THE INVENTION

This invention relates to a method for separating t-amyl alcohol from 2-methyl-1-propanol using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

T-Amyl alcohol and 2-methyl-1-propanol boil six degrees apart and have a relative volatility of 1.08 which makes it impossible to separate them by conventional distillation or rectification. Table 2 shows that with an agent giving a relative volatility of 1.6, only 27 actual plates are required to get 99% purity.

TABLE 2

Theoretical and Actual Plates Required vs. Relative Volatility for t-Amyl Alcohol from 2-Methyl-1-propanol Separation

| Relative Volatility | Theoretical Plates Required At Total Reflux, 99% Purity | Actual Plates Required, 75% Eff. |
|---|---|---|
| 1.3 | 34 | 46 |
| 1.45 | 24 | 32 |
| 1.6 | 20 | 27 |

OBJECTIVE OF THE INVENTION

The object of this invention is to provide a process or method of extractive distillation that will enhance the relative volatility of t-amyl alcohol from 2-methyl-1-propanol in their separation in a rectification column. It is a further object of this invention to identify effective extractive distillation agents that are stable and can be recycled.

SUMMARY OF THE INVENTION

The objects of this invention are provided by a process for the separation of t-amyl alcohol from 2-methyl-1-propanol which entails the use of certain organic compounds when employed as the agent in extractive distillation.

TABLE 3

Effective Extractive Distillation Agents For Separating t-Amyl Alcohol From 2-Methyl-1-propanol

| Compounds | Relative Volatility |
|---|---|
| None | 1.08 |
| 3-Pentanone | 1.3 |
| 2-Pentanone | 1.3 |
| 2,6-Dimethyl-4-heptanone | 1.35 |
| Isophorone | 1.35 |
| Propylene glycol | 1.3 |
| Polyethylene glycol 200 | 1.35 |
| Polyethylene glycol 400 | 1.4 |
| Glycerol | 1.4 |
| Acetol | 1.35 |
| Triethanol amine | 1.35 |
| 2-Amino-2-methyl-1-propanol | 1.45 |
| 1,2-Diaminocyclohexane | 1.5 |
| 1-Methyl piperazine | 1.4 |
| Butyrolactone | 1.3 |
| Pyridine | 1.3 |
| Formamide | 1.4 |
| N,N-Dimethylformamide | 1.3 |
| N,N-Dimethylacetamide | 1.45 |
| 1,2,4-Trimethylbenzene | 1.6 |
| Cyclohexyl amine | 1.45 |
| 2,6-Dimethylmorpholine | 1.3 |

DETAILED DESCRIPTION OF THE INVENTION

I have discovered that certain organic compounds will effectively increase the relative volatility between t-amyl alcohol and 2-methyl-1-propanol during rectification when employed as the agent in extractive distillation. They are 2-pentanone, 3-pentanone, 2,6-dimethyl-4-heptanone, isophorone, propylene glycol, polyethylene glycol 200, polyethylene glycol 400, glycerol, acetol, triethanol amine, 2-amino-2-methyl-1-propanol, 1,2-diaminocyclohexane, 1-methyl piperazine, butyrolactone, pyridine, formamide, N,N-dimethylformamide, N,N-dimethylacetamide, 1,2,4-trimethylbenzene, cyclohexyl amine and 2,6-dimethylmorpholine.

THE USEFULNESS OF THE INVENTION

The usefulness or utility of this invention can be demonstrated by referring to the data presented in Tables 1, 2 and 3. All of the successful agents show that t-amyl alcohol can be separated from 2-methyl-1-propanol by means of extractive distillation and that the ease of separation is considerable.

WORKING EXAMPLE

Example 1

Fifty grams of t-amyl alcohol and 2-methyl-1-propanol and fifty grams of N,N-dimethylacetamide as the extractive distillation agent were charged to a vapor-liquid equilibrium still and refluxed for two hours. The vapor composition was 34.5% t-amyl alcohol, 65.5% 2-methyl-1-propanol; the liquid composition was 26.5% t-amyl alcohol, 73.5% 2-methyl-1-propanol. This is a relative volatility of 1.45.

I claim:

1. A method for recovering t-amyl alcohol from a mixture consisting of t-amyl alcohol and 2-methyl-1-propanol which consists essentially of distilling said mixture consisting of t-amyl alcohol and 2-methyl-1-propanol in the presence of an extractive distillation agent, recovering the t-amyl alcohol as Overhead product and obtaining the 2-methyl-1-propanol and the extractive distillation agent as bottoms product, wherein said extractive distillation agent consists of one material selected from the group consisting of 2-pentanone, 3-pentanone, 2,6-dimethyl-4-heptanone, isophorone, propylene glycol, polyethylene glycol 200, polyethylene glycol 400, glycerol, acetol, triethanol amine, 2-amino-2-methyl-1-propanol, 1,2-diaminocyclohexane, 1-methyl piperazine, butyrolactone, pyridine, formamide, N,N-dimethylformamide, N,N-dimethylacetamide, 1,2,4-trimethylbenzene, cyclohexyl amine and 2,6-dimethylmorpholine.

* * * * *